United States Patent [19]
Shi

[11] Patent Number: 5,998,184
[45] Date of Patent: Dec. 7, 1999

[54] BASKET-TYPE BIOREACTOR

[75] Inventor: Yuan Shi, Milford, Mass.

[73] Assignee: UniSyn Technologies, Inc., Hopkinton, Mass.

[21] Appl. No.: 08/946,884

[22] Filed: Oct. 8, 1997

[51] Int. Cl.[6] .................................................. C12N 11/14
[52] U.S. Cl. ......................... 435/176; 435/328; 435/348; 435/398; 435/400; 435/297.4; 435/299.2; 435/818
[58] Field of Search .............................. 435/297.4, 299.1, 435/299.2, 304.1, 818, 176, 328, 348, 398, 400

[56] References Cited

U.S. PATENT DOCUMENTS

| | | |
|---|---|---|
| 4,889,812 | 12/1989 | Guinn et al. ............................. 435/289 |
| 4,904,601 | 2/1990 | Mano et al. ............................. 435/314 |
| 5,654,197 | 8/1997 | Jem et al. ................................ 435/383 |
| 5,705,390 | 1/1998 | Kadouri et al. ......................... 435/395 |

OTHER PUBLICATIONS

Jager, et al. "Increasing the Rate of Production of Monoclonal Antibodies by Combining a Stirred Reactor With a Hollow Fiber Perfusion System", *Proceedings 4th European Congress on Biotechnology 1987*, vol. 3, pp. 581–584 (Ed., Neijssel, et al.; Elsevier Sci. Pub., Amsterdam, 1987).

*Primary Examiner*—David A. Redding
*Attorney, Agent, or Firm*—Edward S. Irons

[57] ABSTRACT

Improved hollow fiber bioreactor systems and cell culture methods are described. The improvement includes means which may be a novel basket bioreactor for extending the extracapillary space of a conventional hollow fiber bioreactor.

13 Claims, 9 Drawing Sheets

BASKET-TYPE BIOREACTOR

FIELD OF INVENTION

This invention provides a novel bioreactor system and related cell culture methodology.

BACKGROUND OF THE INVENTION

Propagation zone configuration of many known bioreactors imposes constraints on cell growth. For example, conventional hollow fiber bioreactors comprise an intracapillary space (ICS) and an extracapillary space (ECS). Cells are seeded in the ECS for cell growth and production of cell-expressed biomolecules. The cells in the ECS are nourished by nutrients which diffuse across the hollow fiber membrane from media circulated through the ICS. The various disadvantages of conventional hollow fiber bioreactors include:

(1) The growth rate of cells seeded in the ECS is slower than that in static T-flask culture or in the stirred tank system.

(2) Cell masses are immobilized in the hollow fiber bundles with consequent resistance to nutrient diffusability and lower cell viability.

(3) The harvest of cell-expressed biomolecules is limited with consequent lower volumetric biomolecule productivity.

(4) Scale-up of hollow fiber bioreactors implicates complex flow paths because the efficiency of such systems is proportional to the surface area of the hollow fiber membrane and the ratio of the total ICS to the total ECS.

DEFINITIONS

In the specification and claims, the following terms mean:

(1) Bioreactor—Any device or means for the propagation of cells.

(2) Hollow Fiber Bioreactor (HFBR)—A bioreactor which comprises a casing and a hollow fiber matrix; typically the hollow fiber may have a 10 kD–70 kD molecular weight cutoff (MWCO). For example, BR1030 available from UniSyn Technologies, Inc., 25 South Street, Hopkinton, Mass., is a 30 kD MWCO and 10 ft² active surface area for cell growth.

(3) Extracapillary Space (ECS)—The space within the HFBR casing which is not occupied by the hollow fibers.

(4) Extracapillary Space Extension (ECSE)—Any means arranged to supplement or enlarge the ECS of a conventional HFBR.

(5) Extracapillary Media or ECS Medium—Any medium for cell culture in the ECS of a HFBR. The ECS medium may be a supplemented medium, a conditioned medium, a serum free medium, or a protein free medium.

(6) Intracapillary Space (ICS)—The totality of space within the lumens of the hollow fibers in a HFBR.

(7) Intracapillary Media or ICS Medium—Cell culture medium passed through the ICS, i.e., through the lumens of the hollow fibers of a HFBR. ICS media may comprise a basal media, a supplemental media, a serum free media, or a protein free media.

(8) Basket Bioreactor (BB)—Any cell propagation device for use alone or in combination with any other bioreactor, wherein said device comprises a culture medium vessel (basket vessel (BV)) and a perforated basket positioned in the vessel. The screen defines a cell culture zone within the vessel. The basket perforations are sized, e.g., from 50 120 meshes, to provide a substantially free flow of media in the directions indicated by the arrows in FIG. 2. The basket may be made from metal, such as stainless steel, or any synthetic resin suitably resistant to the bioreactor environment. Such resins include certain polyolefins, polycarbonates and the like. The basket may contain a cell supporting material to entrap anchorage independent cells and to immobilize anchorage dependent cells. The basket may have one removable top cover. Alternatively, it may be designed with many covers to provide stacked sub-columns, thereby accommodating the combined use of different supporting materials.

(9) Cell Supporting Material (CSM)—Any material useful to anchor or otherwise immobilize cells cultured in a bioreactor. Representative supporting materials include fibra-cell disks (New Brunswick Scientific Co., Inc.), Cytodex Microcarriers (Pharmacia Biotech) or porous ceramics (Cellex Biosciences, Inc.), sponge, fibers, porous beads, and peptide-coated beads.

(10) Basal Medium—Any cell culture medium which contains essential amino acids and carbohydrates in concentrations appropriate for cell growth; for example, DMEM (Gibco), RPMI (Gibco), F12 (Gibco) and 199 (Gibco).

(11) Medium Supplement—Any material added to a basal medium to enhance cell growth or expression. For example, serum to provide growth factors.

(12) Conditioned Medium—A medium obtained from the same cell culture while cells are being expanded. One form of conditioned medium is a supernatant liquid formed in inoculator cell culture frequently by static culture. See co-pending application Ser. No. 08/840,151 filed Apr. 11, 1997.

(13) OXY10—A commercial hollow fiber oxygenator available from UniSyn Technologies, Inc., 25 South Street, Hopkinton, Mass. The OXY10 may be provided with 0.2 $\mu$m pore size polyethylene hollow fibers woven to form a matrix. The active surface area for gas exchange is 10 ft².

(14) Cell-Pharm 2000 (CP2000)—A commercial hollow fiber bioreactor available from UniSyn Technologies, Inc. The CP2000 may include a HFBR, an oxygenator, a temperature controller, a pH sensor, a gas mixture control capability, an ICS media reservoir, a pump for recirculation of ICS media, a pre-heater, pinch valves, and a peristaltic pump for perfusion of fresh ICS media.

(15) MAB—Monoclonal antibody.

(16) Glucose Uptake Rate (GUR)—The rate at which cultured cells consume glucose, e.g., from the ICS medium in a HFBR. GUR may be expressed (in units of mass per unit time, e.g., gm/day) on the day prior to the current sample as follows:

$$GUR = F(Gf-G) + (V1+VE)(G1-G2) + VE(Ge-G)$$

$$G = (G1+G2)/2$$

where Gf is the glucose concentration in perfusion of ICS media (i.e., 4.5 g/L), G1, the glucose concentration (g/L) in ICS recirculating media on the day prior to the current sample, G2, the glucose concentration (g/L) in ICS recirculating media in the current sample, Ge, the glucose concentration (g/L) in fed ECS media, F, the ICS media feeding rate (L/day), V1, the volume of ICS media in reservoir (L), and VE, the volume of ECS media.

SUMMARY OF THE INVENTION

A major constraint on the efficiency of hollow fiber bioreactors is inefficient diffusability of nutrients such as glucose, amino acids, dissolved oxygen, etc. caused by heterogeneous distribution of dense cell mass surrounding the hollow fiber matrix.

This invention provides a novel hollow fiber bioreactor system which facilitates nourishment and aerobic propagation of cells in a mass density which maintains and may enhance viability. MAB production is increased and MAB concentrations are higher than observed with conventional HFBRs. One important aspect of this invention is a unique basket bioreactor (BB) for use alone or in combination with a known bioreactor type which may be a component of a commercial system, such as a CP2000. The BB comprises a cell culture vessel (BV) and a perforated basket within which a cell mass may be uniformly immobilized, preferably on or within a cell support material.

When the BB is used in combination with a bioreactor, a pump, preferably peristaltic, is used to cycle ECS media between the BB and ECS of the HFBR, thereby eliminating the gradients of nutrients around axial fibers and providing a homogeneous environment for cell growth. This flow also reduces the diffusion resistance on the outside surface of the fibers and improves the diffusion performance, increasing the nutrient mass transfer and the transfer of waste removal.

In the method of the present invention, the ratio of the volume of the basket to volume of BV is preferably 2 to 5. The optimum ratio may vary depending on other operating parameters.

Because the cell supporting material may occupy only to 10% of volume of the basket, the available growth space per cell is significantly enlarged as compared with the ECS of the conventional HFBR. Consequently, the limitation imposed by conventional HFBR configuration on quantity of ECS media is eliminated.

The biomolecules produced by cells can be harvested by changing the direction of the flow through the BB. Generally, the harvest is cell free, and contains a higher concentration and larger volume of the desired biomolecules than that observed with a conventional HFBR.

Valve means may be provided to permit feeding ECS media and the supply of fresh displacement ECS media in the space provided in the BE by the biomolecule harvest.

The invention also provides a method of cell removal from the BB. The basket vessel may be disconnected from the ECS of a HFBR, and the cultured cells are shaken away from the cell supporting material and may be automatically re-suspended in the basket vessel for cell harvest. A cell detachment enzyme, such as trypsin or collagenase, may first be introduced into the basket vessel to facilitate efficient harvesting of anchorage dependent cells.

The system, basket bioreactor and methodology is useful to culture any and all cell types. Such cell types may include insect cells or mammalian cells as such or as transfected with a vector that expresses a recombinant protein, such as transfected CHO cells.

For the culture of cells, e.g., insect cells which, as compared with mammalian cells, may require higher dissolved oxygen concentration or higher cell mass density, a separate hollow fiber oxygenator may be installed within the BB to supply dissolved oxygen directly in the ECS media. The ECS media recirculation can be passed through the ECS of that oxygenator. Air mixed with $CO_2$ passes through the lumens of the oxygenator fibers. This gas flow may protect cells which are suspended in the ECS media from damaging shear forces caused by the media flow which changes in linear velocity when it goes into the lumens of the oxygenating fibers. This method can also be used to raise pH in the ECS media for dense cell culture wherein the flowing air may carry away cell produced by $CO_2$.

The novel basket bioreactor may be combined with any HFBR or with other known bioreactor types, such as stirred tanks, air lifts, ceramic columns, microcarrier suspension, packed beds, fluidized beds, and membranes, to produce cells and cell expression products, such as biomolecules, monoclonal antibodies, recombinant proteins, viruses, viral vectors, peptides, growth factors, and other substances produced by mammalian, transfected mammalian cells, stem cells, insect cells, and plant cells. It can also be developed as a tool for artificial organs, cellular therapy, gene therapy, and pharmacologies.

DETAILED DESCRIPTION OF A PREFERRED EMBODIMENT

Figure 1:
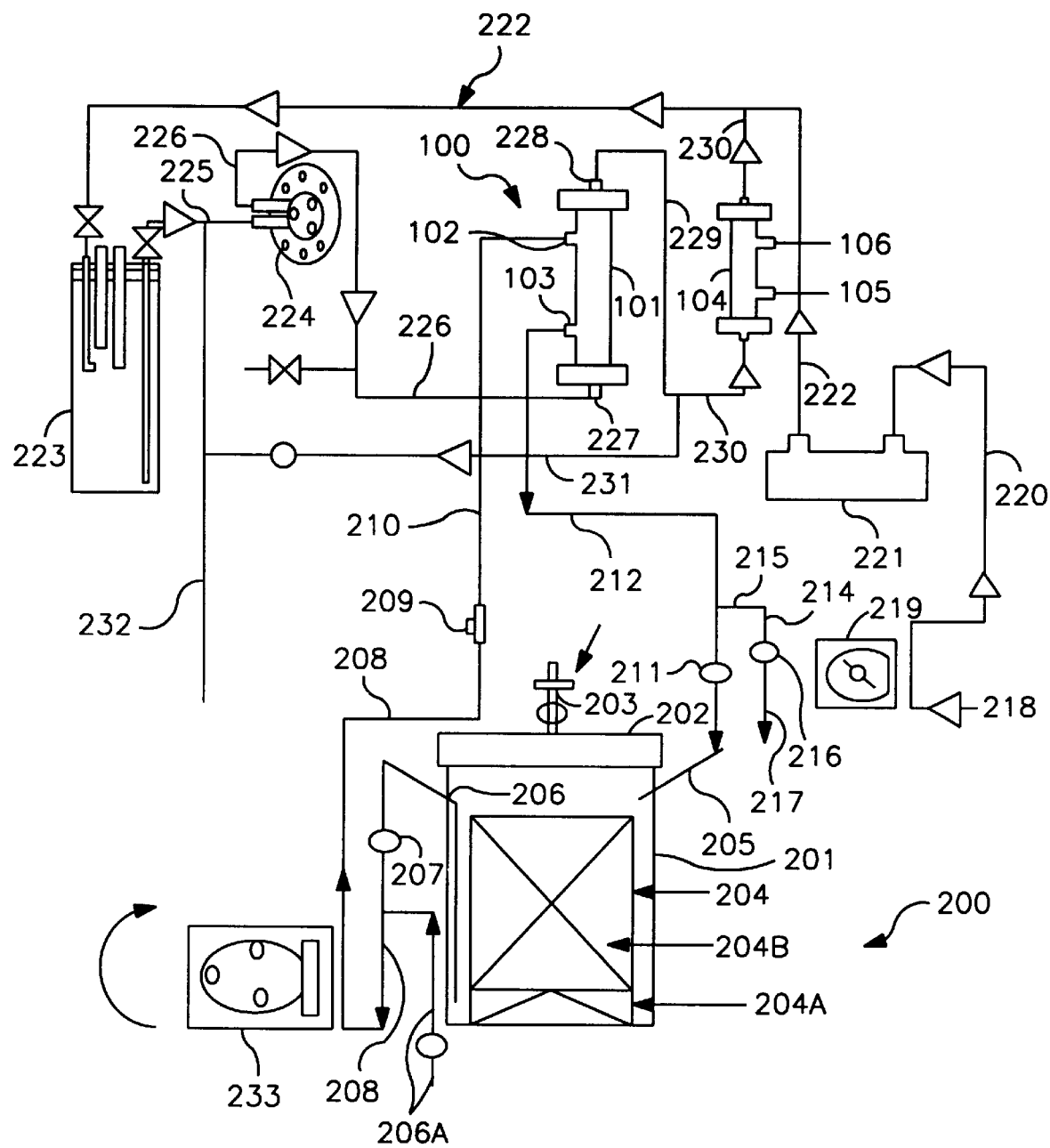
FIG. 1 is a generalized schematic illustration of one bioreactor system of the invention.

The invention may include, as one embodiment, a bioreactor system as schematically illustrated by FIG. 1 that comprises a hollow fiber bioreactor 100, which may be conventional, combined with a basket bioreactor 200.

The hollow fiber bioreactor 100 may comprise a casing 101, an ICS and an ECS defined by a hollow fiber bundle (not shown) positioned in the casing. The hollow fiber bioreactor 100 has an inlet port 102 and an outlet port 103 and an associated oxygenator 104; see, e.g., FIG. 6 of U.S. Pat. No. 5,126,238. OXY10 oxygenators available from UniSyn Technologies, Inc., 25 South Street, Hopkinton, Mass. are appropriate. As shown, the oxygenator 104 has a gas inlet port 105 and a gas outlet port 106.

The basket bioreactor 200, as shown schematically in FIG. 1, includes a basket vessel (BV) 201 having a top 202 and a valved gas filter 203. A basket screen (BS) 204 is positioned on support 204A inside the BV 201 to provide a space 204B between the sidewall of the basket and the basket vessel. The sidewall, top and bottom of the basket 202 may be formed from a synthetic resin or metallic screen material preferably having a mesh size of 50 to 120. The BV 201 may contain a cell culture medium which passes the mesh of the BS. The BV 201 has ports 206 and 205 for the withdrawal and return of fluids. A nutrient medium as shown in FIG. 1 may be introduced into the space 204B through the ECS feed line 206A.

The ECS Loop

The pump 233 circulates ECS medium from the port 206 of the BV 201 through the line 208, the cell harvesting means 209 and the line 210 to the ECS inlet port 102 of the hollow fiber bioreactor 100. The ECS media flows from the exit port 103 of the hollow fiber bioreactor through the line 212 to the inlet port 205 of the basket bioreactor. The line 212 is provided with cell harvesting means 214 which includes line 215, valve 216 and line 217.

The ICS Loop

The ICS medium is fed to the system through line 218, pump 219, line 220, preheater 221, line 222 to recirculation reservoir 223. Pump 224 circulates ICS medium through lines 225 and 226 to the ICS inlet port 227 of the hollow fiber bioreactor 100. The ICS medium exits from the HFBR through port 228 and circulates through line 229 to oxygenator 104 from which it is recirculated to reservoir 223 through lines 230 and 222. Alternatively, ICS medium which passes through the HFBR 100 may be passed through lines 229, 230 and 231 to the ICS waste line 232. Fluid circulation through the line 208 as indicated by the arrows is provided by preferably a peristaltic pump 233.

A Preferred Basket Bioreactor

Figure 2:
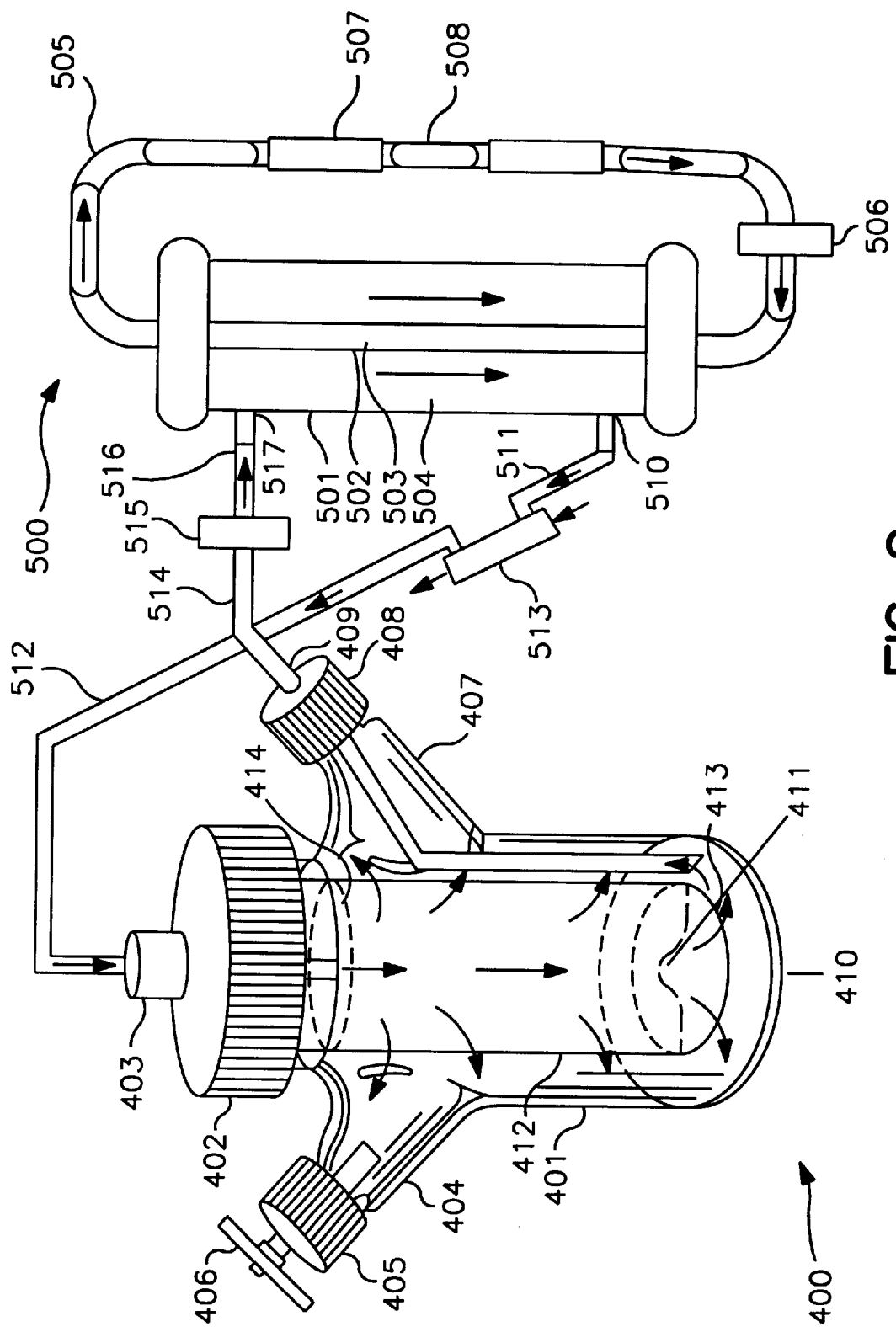
FIG. 2 is a schematic illustration of a flow path of one form of the bioreactor system of the invention.

FIG. 2 shows a preferred embodiment of a basket bioreactor 400 operatively connected to a hollow fiber bioreactor 500, such as CP2000. Referring to FIG. 2, the basket bioreactor 400 may include a basket vessel 401 having a cap 402 provided with a port 403, side arm 404 having a cap 405 provided with a port 406 and side arm 407 having a cap 408 provided with a port 409. The bottom 410 of the basket vessel 401 has a dome shape 411.

A basket 412 formed from synthetic resin or metallic screen material, having a mesh sized to preclude the passage of cells, for example, a mesh size of 50 to 120, is positioned in the basket vessel 401 over the dome 411. As shown in FIG. 2, the sidewall of the basket 412 is spaced from the sidewall of the basket vessel 401. In operation, media flows freely through the mesh of the basket vessel and in the directions indicated by the arrows in FIG. 2. The basket 412 has a sealed bottom 413 and a removable cover 414.

The HF bioreactor 500 has a casing 501, a hollow fiber bundle 502, shown schematically, which provides an ICS 503 formed by the lumens of the fiber positioned in the casing 501 to define an ECS 504.

The hollow fiber bioreactor 500 has a loop 505 for circulation of ICS media. The loop 505 includes a pump 506, an oxygenator 507 (such as OXY10), a medium reservoir 508 which may provide temperature control means. The hollow fiber bioreactor ECS outlet 510 is connected to the inlet port 403 in the cap of the basket bioreactor lines 511 and 512.

FIG. 2 shows an optional second oxygenator 513 connected to lines 511 and 512.

The outlet port 409 of cap 408 on side arm 407 of the basket bioreactor 400 is connected by line 514, pump 515 and line 516 to the ECS inlet port 517 of the hollow fiber bioreactor. The pumps 506 and 515 circulate ECS and ICS media in the directions indicated by the arrow.

Figure 3:
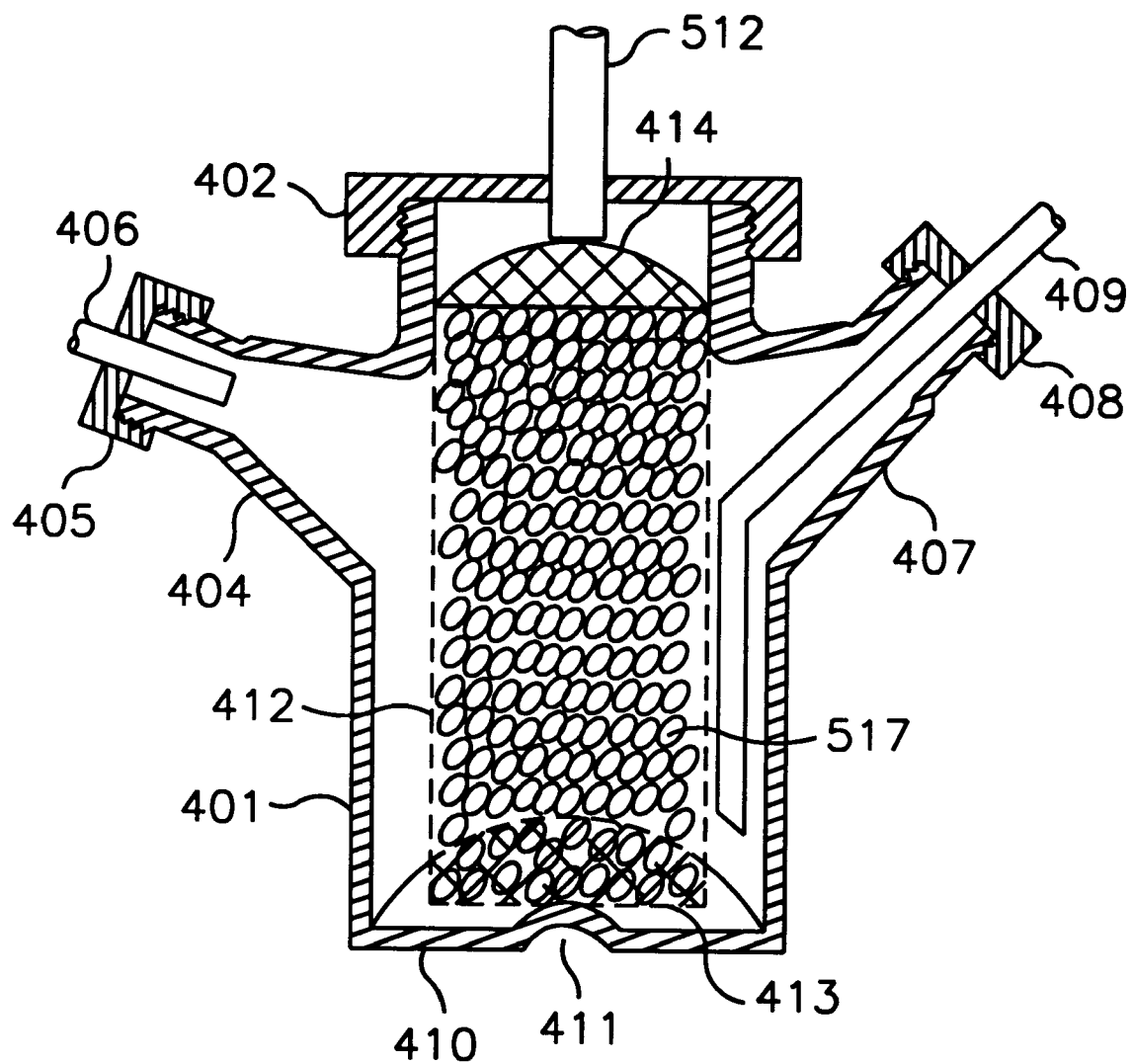
FIG. 3 is a vertical cross-section of the basket bioreactor as shown by FIG. 2 in which the basket contains a cell supporting material.

The basket bioreactor 413 may be filled or packed with cell supporting materials 417 as shown by FIG. 3. Any material which functions to entrap or immobilize or chemically bind cells is included in this invention. Examples of supporting materials presently preferred for use in this invention include:

(1) Flat polyester non-woven fiber disks preferably with cationic charge (positive charge). For example, 6 mm diameter disks supported on polypropylene.

(2) Hydrophilic, e.g., cellulose or polyethylene, fibers and solid tubes and sponges with net binding charge.

(3) Microcarriers, such as agarose, alginate and collagen beads, and which may bear peptides and proteins, such as RGD, fibronectin, charged amino groups and cationic lipids.

(4) Polylysine capsules, etc.

(5) Ceramic particles.

(6) Microporous gelatin.

As shown by FIGS. 1–3, this invention accommodates a basket bioreactor as part of a closed HFBR system to enhance cell growth and cell production rates that are normally limited in the ECS of a HFBR. Viable cells with higher density are uniformly entrapped in the void spaces provided by randomly packed support material 417, e.g., polyester disks (6 mm diameter) and on the surface of the support material, and nourished by ECS media flowing around cells from the outlet of the ECS of the HFBR to the top of the basket.

As shown by the arrows in FIG. 2, the spent media is pumped out from the bottom of the basket vessel to the inlet 516 of the ECS of the HFBR to exchange the combined chemical components by diffusion of an ICS media passing through the hollow fiber lumens across the hollow fiber membranes.

Figure 4:
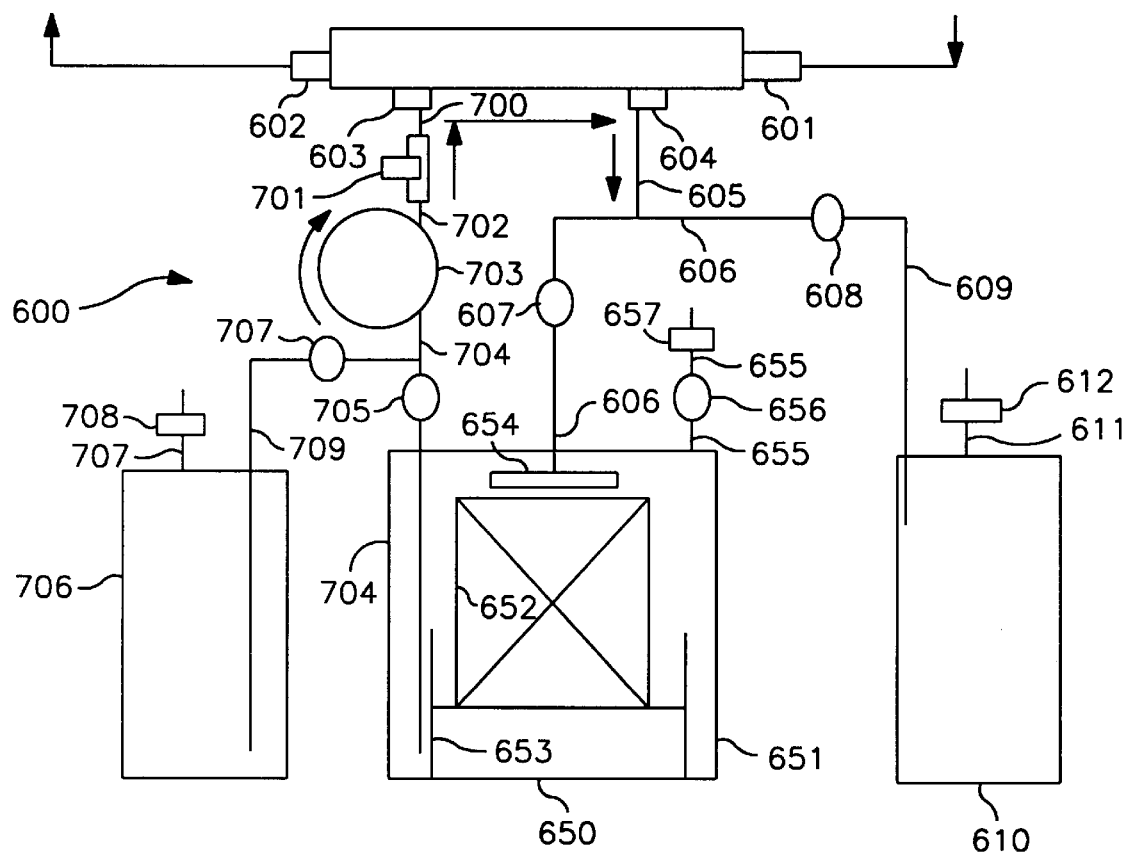
FIG. 4 is a schematic illustration of another form of a bioreactor system of the invention.

Operation of a bioreactor system of the invention is schematically illustrated by FIG. 4. Referring to the figure, the bioreactor system 600 may have a conventional hollow fiber bioreactor 601 with an ICS inlet port 601, ICS outlet port 602, ECS inlet port 603 and an ECS outlet port 604. FIG. 4 includes a schematic basket bioreactor 650 which may have a basket vessel 651, a screen 652, a support 653 for the basket 652 and a flow distributor 654. The basket vessel 651 has a line 655, flow control means 656 and filter 657. ECS outlet port 604 is connected through lines 605 and 606, having flow control means 607 and flow distributor 654 to basket vessel 651.

ECS medium may alternatively pass from ECS outlet port 604 through lines 605 and 606, flow control means 608 and line 609 to harvest bottle 610 provided with line 611 and filter 612.

As also shown by FIG. 4, the ECS inlet port 603 is connected by line 700, sampling means 701, line 702, pump 703, line 704, flow control means 705 to the space between the sidewall of the basket and the basket vessel 601. The FIG. 4 system includes a fresh ECS media container 706 connected by line 707 to filter 708. Line 709 connects container 706 through flow control means 711 and line 710 to line 704.

ECS medium is fed to the FIG. 4 system by closing flow control means 705 and opening flow control means 711 and preferably flow control mens 656. Upon completion of ECS feeding, flow control means 711 and 656 are closed. Flow control means 705 is opened.

To harvest ECS media, flow control means 608 is opened and flow control means 607 is closed. Thereafter, flow control means 656 is preferably opened. After harvest, flow control means 607 is opened, and 608 and preferably 656 are closed.

The basket screen allows media to flow in three dimensions with consequent low pressure drop and low mass transfer resistance within the basket to enhance cell growth rate. The pH, dissolved oxygen level and temperature in the basket may be controlled by adjusting the recycling rates of the ECS media and the ICS media.

Commercial HFBR systems, such as the CP2000, may have a temperature controller to maintain the temperature in the entire closed system and an oxygenator, such as an OXY10, to control pH in both ICS media and ECS media by adjusting the flow rates of $CO_2$ and air and to supply enough dissolved oxygen for cell aerobic propagation. In the preferred method of the invention, the recycling rates of the ICS media and of the ECS media are controlled to minimize the difference in the concentrations of chemicals, such as glucose, lactate, amino acids, ammonia, dissolved oxygen, pH, $CO_2$, and temperature. The dissolved oxygen level may be indirectly determined by a ratio of lactate production rate to glucose uptake rate. Preferably, the ratio can be between 0 to 1 when expressed as gram/gram or 0 to 2 when expressed as mole/mole.

The MAB produced by hybridoma cells is concentrated in recycled ECS media in the BB because of the molecular weight cut off, e.g., 10 kD, of the hollow fibers. Harvesting of MAB may be accomplished by controlling the flow control means to change the flow direction of ECS media when the MAB concentration is increased to the level desired. After harvesting, the empty space in the basket vessel may be quickly filled with the fresh ECS media by controlling the appropriate flow control means.

The level of dissolved oxygen in ECS media can be enhanced by installing a second oxygenator in the ECS recycling loop as shown in FIG. 2 to directly oxygenate cell mass in the basket.

As shown by the examples, two basket vessels with different volumes packed with different amounts of the same or different cell supporting material may be used. For example, one basket may be packed with 20 grams of supporting material (e.g., polyester non-woven fiber disks) and installed with a 1.5 square foot HFBR having a 1.0 square foot oxygenator in the flow path for the culture of hybridoma cells. In such a system, an approximate 43 fold increase in cell expansion has been measured during 7 days. Another basket packed with 30 grams of polyester fiber disks is installed with a 10 square foot HFBR in CP2000 bioreactor instrument having a 10 square foot oxygenator in the flow path, resulting in a 140 fold increase in cell mass during 30 days with about 11 grams of monoclonal antibody produced.

Additional surface area for anchorage dependent cells may be achieved by introducing microcarriers alone or with fiber disks in the basket to provide a mixed matrix. Because the void spaces between randomly packed disks are utilized by microcarriers, the total available surface area for cell attachment may be increased significantly. Suitable microcarriers for this purpose include Cytodex 1, 2 and 3 (Pharmacia Biotech), Arg-Gly-Asp (RGD) peptide coated microcarriers, and others.

EXAMPLE I

Three experiments were conducted to determine the diffusion rate of mass transfer of 1.5 $ft^2$, 10 $ft^2$, and 35 $ft^2$ HFBRs. The speed of flowing fluid through the ICS of the HFBR was set at 142.5 mL/min for the first experiment in CP100 instrument and 900 mL/min for another two experiments in CP2000 instrument. To determine the differences of diffusion rates with and without a flow through the ECS of the HFBR, a variable speed peristaltic pump was employed to provide a constant recirculation through the ECS of the HFBR for each experimental condition. The glucose (Sigma Company) was dissolved in the water and placed in the ICS reservoir to be used as an indicator to determine the glucose concentrations in both sides of the HFBR from time to time. Since each experiment was conducted during 20 minutes, the potential glucose consumption caused by bacteria can be negligible. The temperature was maintained at 37° C. to minimize the deviation of glucose measurement caused by varying temperature during the determination. The glucose concentration is analyzed by using a YSI 2300 STAT plus for glucose/lactate (YSI Co., Inc.)

Figure 7:
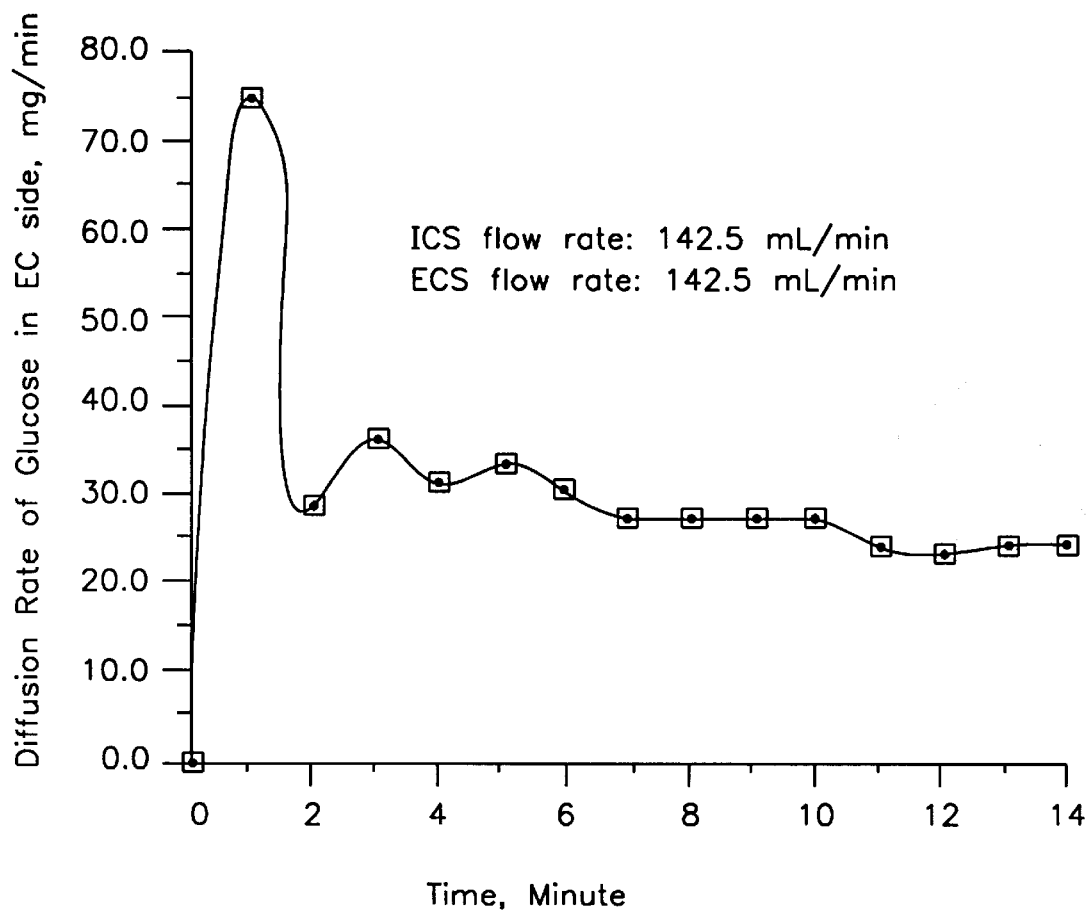
FIG. 7 depicts curves that compare diffusion rates of glucose across the hollow fiber membrane from the ICS to the ECS of a BR130 HFBR with and without a flow of medium through the ECS of the HFBR. The BR130 HFBR has a 1.5 square foot of active surface and a 30 kD molecular weight cut-off (MWCO).
Figure 8:
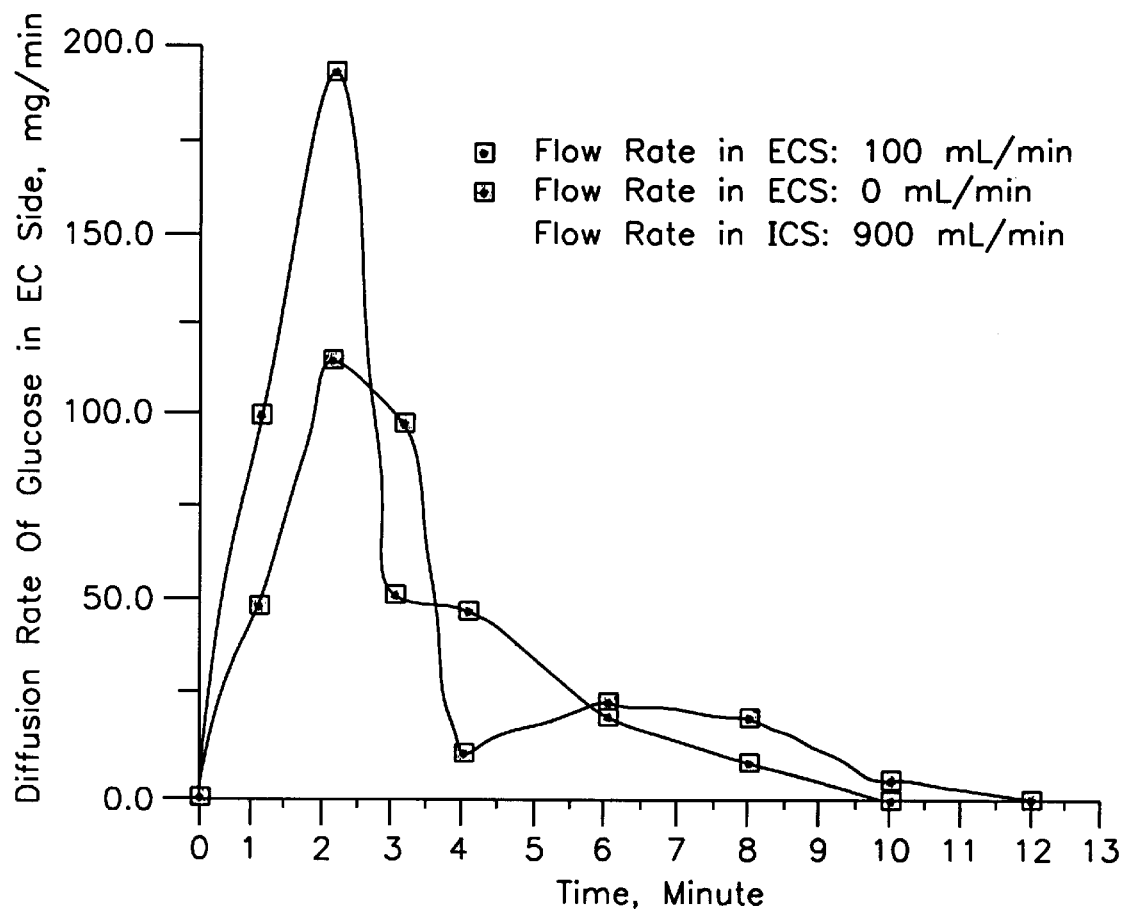
FIG. 8 depicts curves that compare diffusion rates of glucose across the hollow fiber membrane from the ICS to the ECS of a BR1010 HFBR with and without a flow of medium through the ECS of the HFBR. The BR1010 HFBR has a 10 square foot of active surface and 10 kD MWCO.
Figure 9:
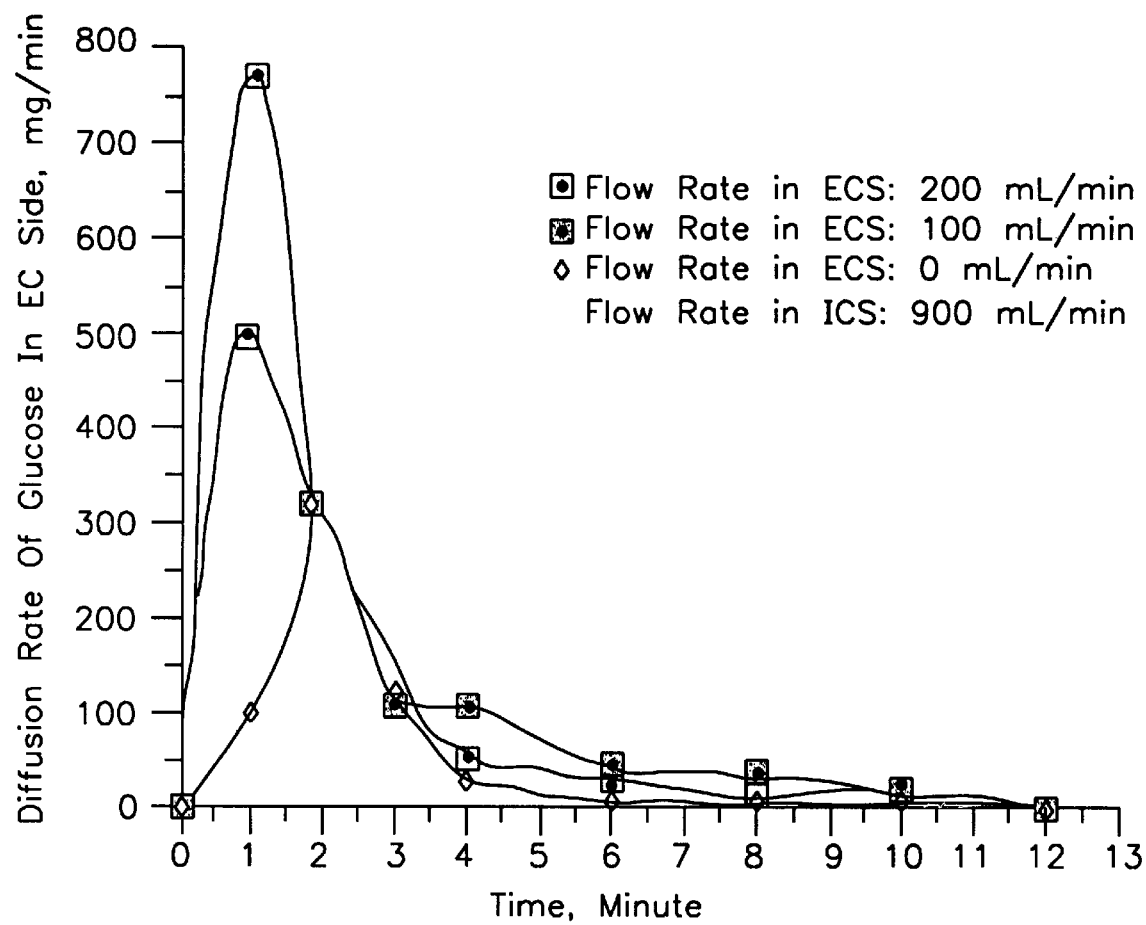
FIG. 9 depicts curves that compare diffusion rates of glucose across the hollow fiber membrane from the ICS to the ECS of a BR3530 HFBR with and without a flow of medium through the ECS of the HFBR. The BR3530 HFBR has a 35 square foot of active surface and 30 kD MWCO.

FIG. 7 shows the rates of glucose diffusion from the ICS to the ECS with both flows at 142.5 mL/min. A peak of diffusion rate appears at first minute in the ECS, that is about 70.5 mg/min. Then, the diffusion rate is kept between 40 to 30 mg/min during 14 minutes. Because the glucose concentration in the ICS dynamically decreases while the glucose concentration in the ECS increases, the driving force to diffuse glucose from higher glucose concentration to lower glucose concentration reduces continuously. However, without the flow through the ECS, the average diffusion rate is determined at about 10 mg/min, and the process of the diffusion appears to be stopped at 10 minutes. Also FIGS. 8 and 9 describe the processes of the diffusion in 10 square foot and 35 square foot HFBRs. The flow rate in the ICS is set at 900 mL/min for both bioreactors, and the rates from 0 to 100 mL/min are set in the ECS for BR1010, and 0 to 200 mL/min are set in the ECS for BR 3530. The results indicate using a suitable flow in the ECS can significantly improve diffusion behavior of nutrients supplied from ICS media and metabolic wastes generated by cells in the ECS media. The optimization of the flow rate in the ECS recirculation has to consider not only the diffusion but also the cell physiological properties such as cell viability, shear force, and cell morphology. The peak of glucose diffusion rate determined in the ECS of BR3530 is at 760 mg/min, which means a possibility of maximal glucose supply at 45.6 grams/hour or 1094 grams/day. Using these diffusion data and the data collected from a static T-flask culture, such as the specific glucose uptake rate and specific MAB production rate, a volume of basket which may be capable of maintaining the cell mass desired may be designed theoretically. Thus, an antibody productivity may be estimated.

EXAMPLE II

Two 30-day cell culture experiments were conducted with 3C11 hybridoma cell line (ATCC, HB8511) that secretes mouse $IgG_1$ monoclonal antibody in a CP2000 bioreactor instrument. In run 1, a BR1010 HFBR (10 square foot of cellulose hollow fibers) was equipped with an OXY10 (10 square foot of polyethylene oxygenator fibers with 0.2 $\mu m$ pore size) for oxygen mass transfer. In run 2, an equivalently sized HFBR (BR 1010) and oxygenator (OXY10) was fitted in CP2000 for 3C11 hybridoma cell culture. A basket vessel with 570 mL of working volume was employed to install a column sized basket. One side arm of basket vessel was connected to the inlet of the ECS of BR1010 and the outlet of the ECS was connected to the top of the basket vessel (see FIG. 1), 30 grams of polyester non-woven fiber disks were randomly packed in the basket to entrap the hybridoma cells. A variable speed peristaltic pump was used to make a recirculation of the ECS media from the basket vessel to the ECS of HFBR. The entire ECS flow path, including a complete basket vessel and tubes, was autoclaved at 121° C. for 45 minutes in the liquid cycle. Final assembly included mounting the BR1010 and OXY10 into the CP2000. The system was flushed with basal media and contamination checked by running 48 hours to ensure sterility and allow for system stability. Two CP2000 instruments maintained temperature at 37° C. The mixed gas went through the OXY10 counter current to the flow of the ICS media through the ICS of the HFBR. Media condition:

(i) ICS media, 5% of fetal bovine serum (FBS) in 1000 mL of basal DMEM. Perfusion of ICS media is started with basal DMEM only.

(ii) ECS media, 10% of FBS in 1000 mL of basal DMEM. In run 1, there is a constant percentage of FBS in the DMEM. In run 2, the percentage of FBS is reduced gradually.

Run 1 was inoculated by $1\times10^9$ viable 3C11 hybridoma cells (over 90% viability) in the ECS of BR1010 by using two sterile, 60 mL syringes with attached 22 gauge needles. One syringe contained 20 mL of ECS media and the cells. The second syringe was empty and used to collect the media displaced during the inoculation.

Run 2 was inoculated by $1\times10^9$ viable 3C11 hybridoma (over 90% viability) in the basket of the ECSE. The basket vessel was filled with 400 mL of complete ECS media and 100 mL of conditioned media. The centrifuged cell pellet was re-suspended into 20 mL of conditioned media and was added into the basket. The basket vessel was incubated for 0.5 hours in a $CO_2$ incubator for cell settlement around the disks packed in the basket. Then, the basket vessel was connected to the ECS of the HFBR with a peristaltic pump. The rate of ICS media recirculation in the run 1 was fixed at 500 mL/min, and the perfusion of ICS media was started with 0.5 L/day at day 5th and increased gradually based on the GUR. However, in run 2, the rate of ICS media recirculation was adjusted from 500 mL/min up to 900 mL/min in order to minimize the differences of glucose and lactate concentrations between the ICS and the ECSE of the HFBR. The perfusion of ICS media was started with 1.0 L/day at day first post the inoculation due to the higher GUR observed. The rate of ECS media recirculation was adjusted from 100 to 200 mL/min for the same purpose described above.

Product harvest was accomplished in a manner similar to the inoculation procedure in the run 1. Harvesting was typically done every other day and 60 mL/each, and the standard operating procedure for this CP2000 system was followed for maintaining cell culture daily. In run 2, the harvesting with 400 mL was done every other day after 14 days of cell culture. The spent media in the ECSE was exchanged by 3 times during first 2 weeks for keeping higher rate of the cell expansion in the basket. To do the harvest, the flow control means indicated in FIG. 1 was operated to change the direction of the flow through in the basket bioreactor. The feeding of the ECS media was completed by controlling the other pinch valves to fill the empty space in the basket bioreactor. The total time spent for harvesting and feeding was less than 5 minutes.

Process parameters in the cell culture systems were set up to monitor glucose, lactate, pH and MAB. For run 2, parameters such as glucose, lactate, pH were tested in both ICS media and ECS media. A YSI glucose/lactate analyzer (YSI Co., Inc.) was employed to determine glucose and lactate concentrations, and a 278 blood gas system (Ciba-Corning, Inc.) was employed to determine pH in the media. These parameters can be used to determine GUR, LPR and MAB productivity. Since one can not directly estimate the cell mass present in the ECS or the basket bioreactor at any given time, GUR and LPR or the ratio of LPR to GUR may be regarded as a means for estimating cell growth for run 1 and run 2. MAB concentration in the harvest was measured by using radial immunodiffusion assays. Initial perfusion rate of the ICS media was started at 0.5 L/day and was increased step by step and the maximized up to 5 L/day for run 1 and 10 L/day for run 2 according to either the glucose concentration (when it fell as low as 2.5 g/L) or lactate concentration (when it reached as high as 20 mM).

Figure 5:
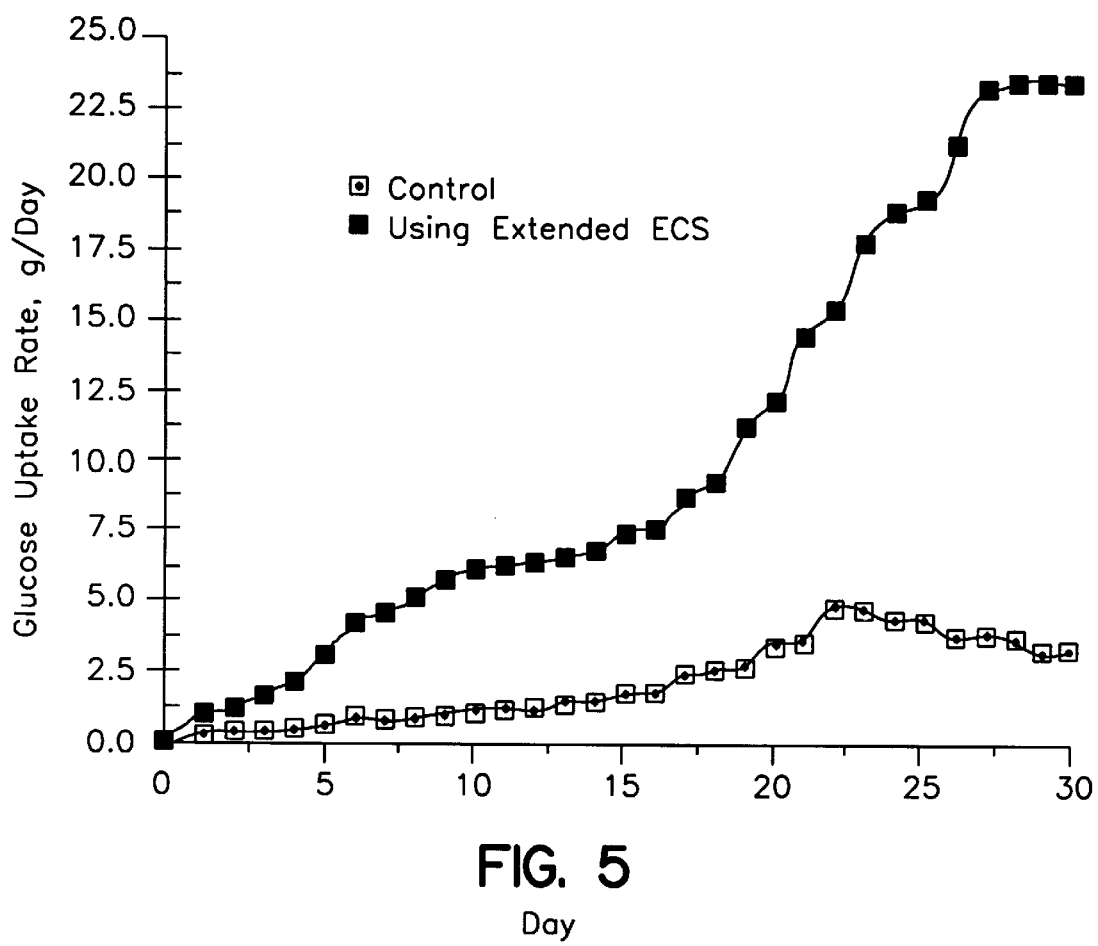
FIG. 5 depicts bar graphs that compare volumetric productivity of antibody by a typical cell line (3C11 hybridoma (ATCC, HB8511)) over a 30-day time period in a 10 square foot HFBR using a conventional operation manner and in a 10 square foot HFBR in combination with a basket bioreactor.
Figure 6:
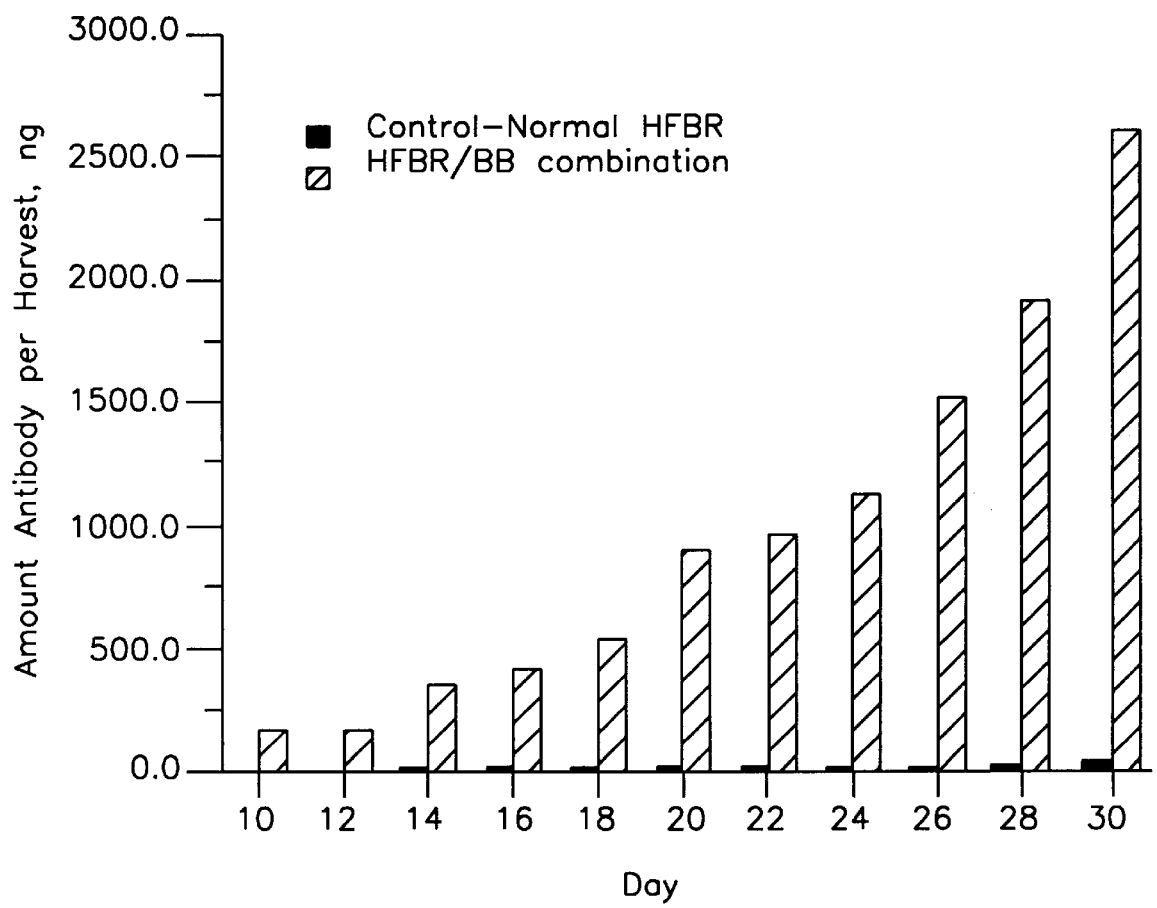
FIG. 6 depicts curves that compare glucose uptake rates (GUR) of 3C11 hybridoma (ATCC, HB8511) in a 10 square foot HFBR operated in a conventional manner alone and in combination with a basket bioreactor.

The MAB production level per harvest in run 1 and run 2 for 3C11 cells are compared to FIG. 5. At day 28th, a daily harvest at 2000 mg of $IgG_1$ was achieved in run 2 and about 2700 mg of $IgG_1$ at day 30th. The cumulative MAB production in run 2 was 10.7 grams during 30 days and only 160 mg in run 1. FIG. 6 shows the GURs in run 2 versus that in run 1 (control) for 3C11 hybridoma cells. A significant increase of glucose uptake indicates there is no lag phase of cell growth in the ECSE system after cell seeded, which is found in normal HFBR and taken a longer period of time (about 2 more weeks) before a production level appears. These results suggest that using a basket to entrap hybridoma can reduce the resistance of mass transfer across the hollow fiber membrane for cell growth. The recirculation of ECS media keeps a uniform environment surrounding the dense cell mass with minimized gradients of either nutrients or metabolic wastes. This results in cells growing more efficiently and more MAB production. Table 1 summarizes the process parameters from these two runs.

TABLE 1

Comparison of Process Parameters of a Hollow Fiber Bioreactor Combined with a Basket Bioreactor vs. a Normal Hollow Fiber Bioreactor

|  | Normal Hollow Fiber Bioreactor | Hollow Fiber with Extended ECS Bioreactor |
| --- | --- | --- |
| Culture System | CP2000/BR1010/OXY10 | CP2000/BR1010/OXY10 |
| ECS Volume | 100 mL | 670 mL |
| Cell Line | 3C11 Hybridoma | 3C11 Hybridoma |
| Cells Inoculated | $1 \times 10^9$ Viable Cells | $1 \times 10^9$ Viable Cells |
| Time of Period | 30 Days | 30 Days |
| Cell Growth Phase | 30 Days | 14 Days |
| Production Phase | 0 Days | 16 Days |
| Harvest Frequency | Every Two Days | Every Two Days |
| Per Harvest Volume | 60 mL | 400 mL |
| Average MAB Concentration | 0.19 mg/mL | 2.03 mg/mL |
| Total MAB Produced | 159.4 mg | 10,737 mg |
| ECS Media Spent | 820 mL | 5290 mL |
| ICS Media Spent | 30.6 L | 175.5 L |
| Cell Viability at Day 30th | 21% | 77% |
| Total Cells | $4 \times 10^{10}$ | $1.4 \times 10^{11}$ |
| Cost Efficiency of Production Spent | 0.35 mg MAB/$1.0 | 10.3 Mg MAB/$1.0 (Media + Parts) |

EXAMPLE III

A 7-day cell culture experiment was conducted with 3C11 hybridoma cell line in a CP100 bioreactor system with BR130 (1.5 square foot HFBR with 30 kD MWCO) and OXY1 (1.0 square foot polyethylene oxygenator). A basket vessel with 500 mL of working volume was connected into the ECS of BR130. The ECS media in the vessel was pumped through the ECS counter current to the flow of the ICS media through the ICS of BR130 and back to the basket vessel. The basket in the vessel was randomly packed with 20 grams of fiber disks. The rate of cell expansion and cell viability in the ECSE were determined at the end of the experiment.

A peristaltic pump assembly was used with two pump heads to provide the identical flow rate one for the recirculation of ICS media and the other for the ECS media. The air and $CO_2$ were mixed and flowed through the OXY1 to control the pH in media in both sides of the HFBR, and to supply enough dissolved oxygen for cell respiration.

The experiment was run by $1.0 \times 10^8$ viable 3C11 hybridoma cells (over 90% viability) in the basket of the ECSE. The basket vessel was filled with 400 mL of complete ECS media and 100 mL of conditioned media. The centrifuged cell pellet was re-suspended into 20 mL of conditioned media and was pipetted into the top of the basket. The basket vessel was incubated for 0.5 hours in a $CO_2$ incubator for cell settlement around the disks packed in the basket. Then, the basket vessel was connected to the ECS of the HFBR with a peristaltic pump.

Media conditions:
(i) ICS media, 5% FBS in 1000 mL of DMEM. The perfusion is started with basal DMEM.
(ii) ECS media, 10% FBS in 1000 mL of DMEM.

The ICS media exchange was started at day first after cell seeding due to the higher GUR found. Normally, the perfusion rate was set 1–2 L per day during the period of 7 days. No ECS media was exchanged during 7 days.

Process parameters in the cell culture system were set up to monitor glucose, lactate, pH in both sides of the media. A YSI glucose/lactate analyzer was employed to determine glucose and lactate, and a 278 blood gas system (Ciba-Corning, Inc.) Was employed to determine pH in the media. These parameters can be used to give GUR and LPR. Since one cannot directly estimate the cell mass present in the ECSE at any given time, GUR and LPR or the ratio of LPR to GUR may be regarded as a means for estimating cell growth within the run.

The experiment was terminated at day 7th to determine the cell mass and cell viability. To harvest cells from the ECSE, the power of the system was turned off, and the basket vessel (extended ECS) was manually and gently shaken for 2 minutes, entrapped hybridoma cells were found most in suspension. The cell suspension was immediately poured out from the side arm of the basket vessel to count cells and cell viability. In order to determine the recovery of cell harvest, a 500 mL of basal media was added into the basket vessel from the side arm after cell harvest. Then, the packed disks and media were removed and placed into a beaker. After stirring media with disks for 1 minute, cell count was done again.

The total cell number was measured at $4.3 \times 10^9$ which was about 43 fold expansion in cell mass based on $1.0 \times 10^8$ cells in inoculation. The cell viability was at 88%. The recovery of cell harvest was at 91.6%. The average GUR from the run was at 2.84 gram/day. As a reference, an average GUR at 0.25 g/day during 7 days was compared from a previous run with the same cell line and number in inoculation in the CP100 with BR130 and OXY1. A technical summary is listed in Table 2.

TABLE 2

Process Parameters of a Hollow Fiber Bioreactor Combined with a Basket Bioreactor

| | |
|---|---|
| Bioreactor | Cell Pharm 100 with BR130 and OXY1 |
| Extended ECS | 500 mL |
| Cell Line | Hybridoma 3C11 (ATCC HB8511) |
| Period of Time | 7 Days |
| Inoculation | $1 \times 10^8$ Viable Cells and 93% of Viability |
| Major Cell Harvest | $39.4 \times 10^8$ Viable Cells and 88.7% of Viability |
| Second Cell Harvest | $3.6 \times 10^8$ Viable Cells and 87.9% of Viability |
| Recovery of Cell Harvest | 91.6% (Major harvest/total harvests) |
| Cell Expansion | 43.0 fold ($39.4 \times 10^8 + 3.6 \times 10^8$) |
| Volume of Cell Suspension | 500 mL (in major harvest) |
| Cell Concentration | $7.9 \times 10^6$ viable cells/mL (in major harvest) |
| ICS Media Used | 7 L |
| ECS Media Used | 500 mL |

I claim:

1. A bioreactor which comprises:
   (i) a vessel which may contain a cell culture medium,
      wherein said vessel comprises a vessel sidewall and means adjacent the top of said vessel sidewall for removing culture medium from said vessel;
   (ii) a basket positioned within said vessel,
      wherein said basket comprises a perforated basket sidewall, and
      wherein said basket is sized to provide a space between said vessel sidewall and said perforated basket sidewall; and
   (iii) means for the introduction of culture media downwardly into the top of said basket,
      wherein said downwardly introduced culture media may pass through said perforations in said basket sidewall and into said space between said basket sidewall and said vessel sidewall and be removed from said bioreactor through said removal means adjacent the top of said vessel sidewall.

2. The claim 1 bioreactor, wherein said basket (ii) contains a cell support material.

3. The claim 1 or claim 2 bioreactor, wherein said basket (ii) is positioned in said vessel and occupies from about 40% to about 50% of the volume of said vessel.

4. A bioreactor which comprises:
   (i) a vessel which may contain a cell culture medium, wherein said vessel has a vessel sidewall;
   (ii) a basket positioned within said vessel,
      wherein said basket has a basket sidewall, and
      wherein said basket is sized to provide a space between said vessel sidewall and said basket sidewall when said basket is positioned within said vessel,
      wherein said basket is formed at least in part from a material having holes sized to provide media flow therethrough;
   (iii) a cell culture media enrichment means;
   (iv) means for passing at least partially spent cell culture media from said vessel through said culture media enrichment means, and
   (v) means for introducing said enriched cell culture medium into said vessel.

5. The claim 4 bioreactor wherein said element (iii) culture medium enrichment means is the extracapillary space of an operating hollow fiber bioreactor.

6. A bioreactor system which comprises:
(i) a hollow fiber bioreactor which has an extracapillary space and an intracapillary space wherein said hollow fiber bioreactor has a first port for the introduction of cell culture media into said extracapillary space and a second port for the withdrawal of at least partially spent cell culture media from said extracapillary space;
(ii) a basket bioreactor wherein said basket bioreactor comprises
  (a) a vessel which may contain a cell culture medium, wherein said vessel has a vessel sidewall;
  (b) a basket positioned within said vessel,
    wherein said basket has a basket sidewall, and
    wherein said basket is sized to provide a space between said vessel sidewall and said basket sidewall when said basket is positioned in said vessel,
    wherein said basket is formed at least in part from a material having holes sized to provide media flow therethrough; and
(iii) means for circulating at least partially spent medium from said vessel of said basket bioreactor through said extracapillary space of said hollow fiber bioreactor to said vessel of said basket bioreactor.

7. The claim 6 bioreactor system wherein said basket is formed at least in part from a screen material having a mesh size of 50 to 120.

8. The claim 6 bioreactor system further comprising:
(iv) means for harvesting cultured cells or the expression products of cultured cells.

9. The claim 6 or claim 8 bioreactor system where the ratio of the volume of said element (ii) basket to the volume of said extracapillary space of said hollow fiber bioreactor is from about 3 to about 12.

10. A method for culturing cells which comprises:
(i) providing a hollow fiber bioreactor
  wherein said hollow fiber bioreactor has an extracapillary space and an intracapillary space;
(ii) circulating an extracapillary space medium through said extracapillary space of said hollow fiber bioreactor wherein said extracapillary space medium may contain cells which propagate therein when said hollow fiber bioreactor is operated;
(iii) withdrawing at least a portion of said circulating extracapillary space medium from said extracapillary space of said hollow fiber bioreactor;
(iv) circulating said portion of said circulating extracapillary space medium withdrawn in step (iii) to a second bioreactor,
  wherein said second bioreactor comprises a cell culture vessel, and
  wherein diffusability of cell nutrients in said cell culture vessel is enhanced as compared with the diffusability of said cell nutrients in said extracapillary space of said first hollow fiber bioreactor.

11. The claim 10 method wherein said extracapillary medium containing cells is passed from said extracapillary space of said first hollow fiber bioreactor to said cell culture vessel of said second basket-type bioreactor
  wherein said cells propagate in said cell culture vessel,
  wherein said extracapillary medium present in said cell culture vessel of said basket bioreactor is at least partially spent by said cell propagation, and
  wherein said at least partially spent extracapillary medium is circulated from said cell culture vessel to and through said extracapillary space of said first hollow fiber bioreactor.

12. The claim 11 method, wherein fresh cell culture medium is passed through the intracapillary space of said first hollow fiber bioreactor concurrently with said circulation of said at least partially spent extracapillary medium through said extracapillary space of said first hollow fiber bioreactor.

13. The claim 10 method, wherein said cells which may be contained in said extracapillary medium are mammalian cells, insect cells, transfected mammalian cells (e.g., CHO cells) which express a recombinant protein or stem cells.

* * * * *